US012635918B2

(12) United States Patent
Holmer et al.

(10) Patent No.: US 12,635,918 B2
(45) Date of Patent: May 26, 2026

(54) MEASURING PARTICLE DENSITY IN A FLUID INSIDE A TUBING

(71) Applicant: GAMBRO LUNDIA AB, Lund (SE)

(72) Inventors: Mattias Holmer, Lund (SE); Jonas Alson, Lund (SE); Erik Karlsson, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 615 days.

(21) Appl. No.: 18/015,401

(22) PCT Filed: Jun. 21, 2021

(86) PCT No.: PCT/EP2021/066750
§ 371 (c)(1),
(2) Date: Jan. 10, 2023

(87) PCT Pub. No.: WO2022/008213
PCT Pub. Date: Jan. 13, 2022

(65) Prior Publication Data
US 2023/0255522 A1 Aug. 17, 2023

(30) Foreign Application Priority Data
Jul. 10, 2020 (SE) .................................... 2050882-6

(51) Int. Cl.
*A61B 5/1455* (2006.01)
*A61B 5/00* (2006.01)
*A61B 5/145* (2006.01)

(52) U.S. Cl.
CPC ........ *A61B 5/14546* (2013.01); *A61B 5/1455* (2013.01); *A61B 5/4836* (2013.01)

(58) Field of Classification Search
CPC .................................................... A61B 5/1455
See application file for complete search history.

(56) References Cited

U.S. PATENT DOCUMENTS

2009/0078047 A1 3/2009 Dam
2010/0022907 A1 1/2010 Perez-Velazquez et al.
(Continued)

FOREIGN PATENT DOCUMENTS

CN 101868694 5/2014
CN 107850536 3/2018
(Continued)

OTHER PUBLICATIONS

International Search Report for related International Application No. PCT/EP2021/066750; action dated Jan. 13, 2022; (3 pages).
(Continued)

*Primary Examiner* — Marjan Fardanesh
(74) *Attorney, Agent, or Firm* — K&L Gates LLP

(57) ABSTRACT

An optical detection apparatus is arranged to detect particles in a fluid flowing through a tubing portion of transparent or translucent material. The apparatus comprises a holder for the tubing portion; a light emitting device configured to irradiate a target volume inside the tubing portion when arranged in the holder; and at least one light receiving device configured to receive light from the target volume when irradiated by the light emitting device and generate one or more time-dependent output signals indicative of the received light. A computation device is configured to determine a parameter indicative of temporal variability in the one or more time-dependent output signals and estimate the density based on the parameter, which has been found to be robust to structural differences between tubings and allows the apparatus to be deployed without calibration.

19 Claims, 5 Drawing Sheets

(56)                    References Cited

U.S. PATENT DOCUMENTS

| 2018/0193546 A1 | 7/2018 | Gerber et al. |
| 2018/0201527 A1 | 7/2018 | Nagao et al. |
| 2021/0186433 A1* | 6/2021 | Yu ........................ A61B 5/1455 |

FOREIGN PATENT DOCUMENTS

| WO | 2014047608 A1 | 3/2014 |
| WO | 2019118929 A1 | 6/2019 |

OTHER PUBLICATIONS

Written Opinion for related International Application No. PCT/EP2021/066750; action dated Jan. 13, 2022; (8 pages).

* cited by examiner

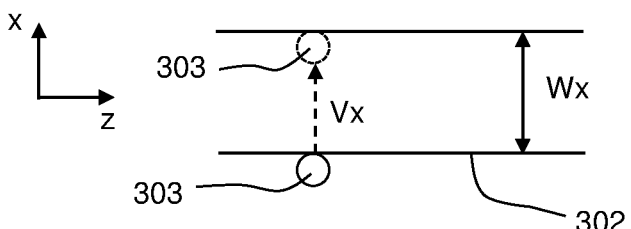
FIG. 3B
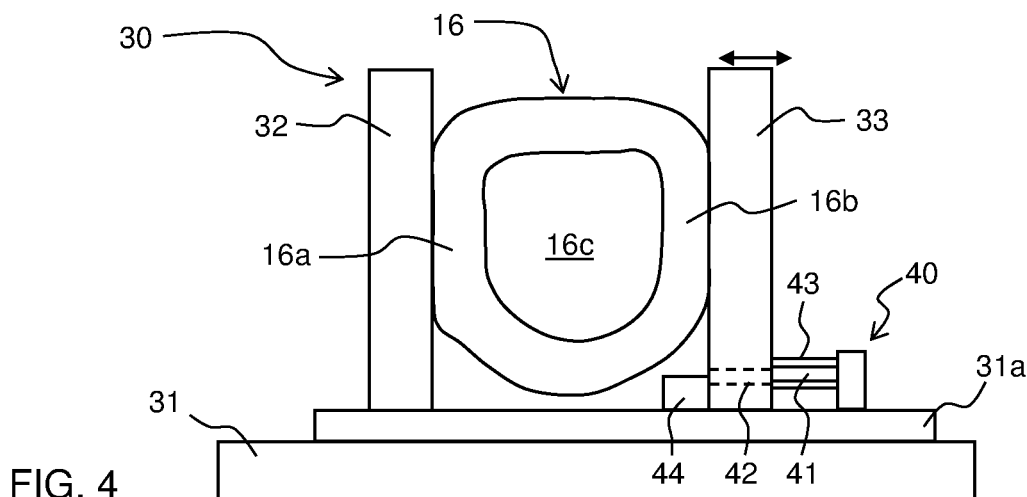
FIG. 4
500
501 — ARRANGE TUBING PORTION IN HOLDER
502 — OPERATE LIGHT EMITTING DEVICE TO IRRADIATE TARGET VOLUME
503 — OPERATE LIGHT RECEIVING DEVICE(S) TO RECEIVE LIGHT FROM TARGET VOLUME
504 — ESTIMATE DENSITY OF PARTICLES BASED ON TEMPORAL VARIABILITY IN OUTPUT SIGNAL(S) FROM LIGHT RECEIVING DEVICE(S)
505 — EVALUATE/PRESENT/STORE ESTIMATED DENSITY OF PARTICLES
FIG. 5

MEASURING PARTICLE DENSITY IN A FLUID INSIDE A TUBING

PRIORITY CLAIM

This application is a national phase entry of PCT/EP2021/066750, filed Jun. 21, 2021, which claims priority to Swedish Patent Application No. 2050882-6, filed Jul. 10, 2020, the entire disclosures of which are incorporated by reference herein.

TECHNICAL FIELD

The present disclosure relates generally to measurements of particle density in fluids, and in particular to optical techniques for measuring the particle density through a tubing. The present disclosure is particularly, but not exclusively, suited for measuring the density of white blood cells in effluent from peritoneal dialysis, for example for assessment of the risk for infection or inflammation.

BACKGROUND ART

Inflammation in the peritoneum is common among patients undergoing peritoneal dialysis (PD). Early detection of infection or inflammation ("peritonitis") is essential to avoid suffering and therapy drop-out. Basically, there are two modalities for carrying out PD: automated peritoneal dialysis (APD) and a manual non-automated procedure denoted continuous ambulatory peritoneal dialysis (CAPD). In CAPD, infection may be detected by visual inspection of effluent bags in which spent dialysis fluid ("effluent") is collected. A cloudy effluent bag is a sign of peritonitis. The cloudiness is caused by increased presence of white blood cells (WBCs) caused by the infection. In APD, the effluent is often passed through an effluent line directly to the drain, and no visual inspection is possible. The infection is therefore detected late, when other signs such as stomach pain appear, and the peritoneum may be damaged.

U.S. Pat. No. 6,228,047 proposes an effluent detector, which is arranged on the effluent line and comprises a light source and a light detector. If the effluent is cloudy when the dialysis fluid is emptied from the peritoneal cavity, the light beam to the light detector is diffused and onset of peritonitis may be signaled.

The prior art also comprises US2008/0045884 and US2008/0183127 which propose to detect peritonitis by measuring the amount of light scattered from a laser beam, which is transmitted through a dedicated transparent measurement chamber that is installed in the effluent line.

It is desirable to provide an optical technique that is applicable to measure particle density through regular tubings of transparent or translucent material. However, there are practical obstacles to applying optical techniques for this purpose. One obstacle is that the tubing wall will scatter incoming light and thereby cause a background signal that makes quantitative measurements difficult. The amount of scattering may differ between tubings, even tubings that are seemingly identical. This scattering will be enhanced if the tubing wall is made of translucent material. Further, the optical properties of the tubing may vary between different locations on the tubing. For example, the tubing may exhibit ridges, grades, lines or other markings that are formed during manufacture, such as in an extrusion process or by rollers. In another example, the tubing may be unevenly frosted on its outside. Another obstacle is that the tubing, if it has a curved cross-sectional shape, may refract light that enters and leaves the tubing. By this refraction, small shifts in the positioning of the tubing may result in large changes in detected signals. All in all, an optical technique that is applied for measuring particle density on ordinary tubing is likely to suffer from a lack of reproducibility and reliability unless the optical technique is carefully calibrated, which is time-consuming and may require operator intervention.

SUMMARY

It is an objective to at least partly overcome one or more limitations of the prior art.

One objective is to provide an optical technique for measuring particle density in a fluid through a tubing.

Another objective is to provide such an optical technique with an improved immunity to variations in properties of the tubing.

A further objective is to provide such an optical technique requiring a minimum of operator intervention.

Yet another objective is to provide an optical technique for use in detection of peritonitis.

One or more of these objectives, as well as further objectives that may appear from the description below, are at least partly achieved by an optical detection apparatus and a method according to the independent claims, embodiments thereof being defined by the dependent claims.

A first aspect is an optical detection apparatus for detecting particles in a fluid flowing through a tubing comprising a tubing portion of transparent or translucent material. The optical detection apparatus comprises a holder for the tubing portion; a light emitting device configured to irradiate a target volume inside the tubing portion when arranged in the holder; and at least one light receiving device configured to receive light from the target volume when irradiated by the light emitting device and generate one or more time-dependent output signals indicative of the received light. The optical detection apparatus further comprises a computation device configured to process the one or more time-dependent output signals to estimate a density of the particles in the fluid, wherein the computation device, to estimate the density, is configured to determine a parameter value indicative of temporal variability in the one or more time-dependent output signals.

A second aspect is a method for detecting particles in a fluid flowing through a tubing comprising a tubing portion of transparent or translucent material. The method comprises: arranging the tubing portion in a holder; operating a light emitting device to irradiate a target volume inside the tubing portion as arranged in the holder; operating at least one light receiving device to receive light from the target volume when irradiated by the light emitting device and to generate one or more time-dependent output signals indicative of the received light; and estimating a density of the particles in the fluid by processing the one or more time-dependent output signals, wherein the estimating comprises determining a parameter value indicative of temporal variability in the one or more time-dependent output signals.

A third aspect is an apparatus for automated peritoneal dialysis comprising the optical detection apparatus of the first aspect.

The foregoing aspects are based on the surprising finding that the temporal variability in the respective time-dependent output signal increases with increasing particle density in the fluid, at least for low particle densities, such as below 1000-2000 particles per microliter. The temporal variability has furthermore been found to be relatively robust to variations in optical properties of the tubing, thereby mitigating the need for calibration and associated operator intervention.

The utility at low densities, combined with a finding that the temporal variability represents particle density for particles with a size comparable to white blood cells, makes the first and second aspect applicable for detection of signs of infection or inflammation, for example peritonitis, in effluent from PD therapy.

Still other objectives and aspects, as well as embodiments, features, advantages and technical effects may appear from the following detailed description, from the attached claims as well as from the drawings.

BRIEF DESCRIPTION OF THE DRAWINGS

Embodiments will now be described in more detail with reference to the accompanying drawings.

FIG. 3B illustrates a particle passing a light beam generated by the optical detection apparatus.

FIG. 4 is a side view of an example holder in engagement with a tubing portion.

FIG. 5 is a flow chart of an example optical detection method.

DETAILED DESCRIPTION OF EXAMPLE EMBODIMENTS

Figure 1:
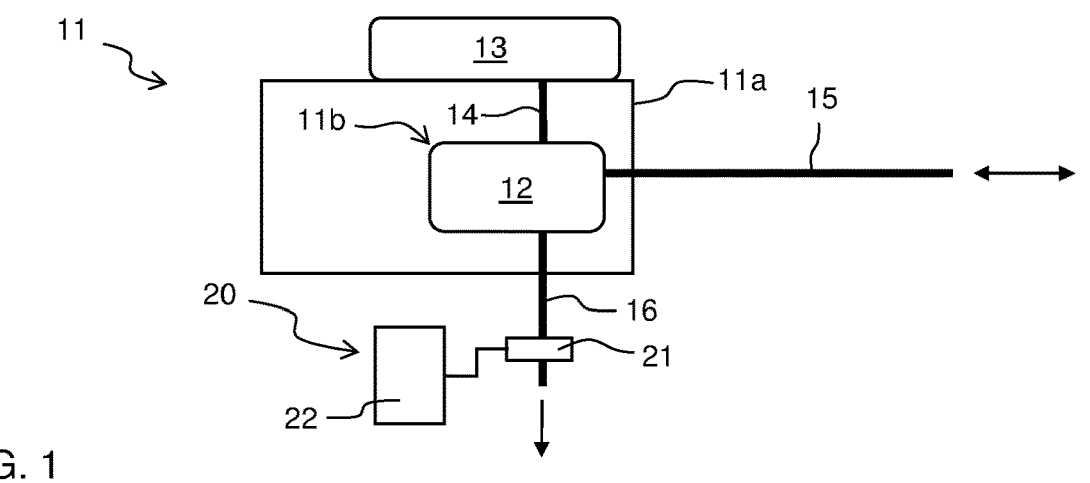
FIG. 1 is a side view of an example arrangement for peritoneal dialysis comprising an optical detection apparatus.

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal requirements.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments. The term "and/or" includes any and all combinations of one or more of the associated listed items.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure.

Well-known functions or constructions may not be described in detail for brevity and/or clarity. Unless otherwise defined, all terms (including technical and scientific terms) used herein have the same meaning as commonly understood by one of ordinary skill in the art to which this disclosure belongs.

Like reference signs refer to like elements throughout.

Embodiments will be described with reference to deployment in conjunction with automated peritoneal dialysis ("APD") therapy. In peritoneal dialysis (PD), dialysis fluid is infused into a patient's peritoneal cavity. This cavity is lined by the peritoneal membrane ("peritoneum") which is highly vascularized. Substances are removed from the patient's blood by diffusion across the peritoneum into the dialysis fluid. Excess fluid (water) is also removed by osmosis induced by a hypertonic dialysis fluid. Automated peritoneal dialysis ("APD") is performed by an APD machine, which is operable to automatically perform one or more treatment cycles including fill, dwell and drain phases, for example while the patient sleeps. The APD machine is fluidly connected to an implanted catheter, to a source or bag of dialysis fluid and to a fluid drain. The APD machine is operated to pump fresh dialysis fluid from the source, through the catheter, into the patient's peritoneal cavity and to allow the dialysis fluid to dwell within the cavity for the transfer of waste, toxins and excess water to take place. The APD machine is then operated to pump spent dialysate from the peritoneal cavity, through the catheter, to the drain.

FIG. 1 is a schematic elevated side view of an arrangement 11 for peritoneal dialysis. The arrangement 11 comprises an APD machine 11*a*, commonly known as an "APD cycler". The arrangement further comprises a disposable unit 11*b* mounted onto the APD cycler 11*a*. The APD cycler 11*a* comprises a combination of a control system, sensors and actuators to properly move fluid inside a hydraulic circuit of the disposable unit 11*b*. Although not shown in FIG. 1, the APD cycler 11*a* may also comprise a user interface for input/output of data. The disposable unit 11*b* comprises a cassette 12, as well as a set of tubes ("tubing set") connected to the cassette 12. In the illustrated example, the tubing set includes a container line 14 terminating in a container 13 configured for holding a treatment fluid ("dialysis fluid"). The container 13 may be in the form of a collapsible bag to be positioned, for example, in a dedicated tray on the APD cycler 11*a*. The container 13 may be delivered as a ready-made bag of dialysis fluid, or the container 13 may be filled by dialysis fluid prepared on-line by the APD cycler 11*a* or a separate machine (not shown), for example by mixing one or more concentrates with water.

The APD cycler 11a may comprise a heater (not shown) for heating the treatment fluid before it is supplied to the patient. The tubing set further comprises a patient line 15 for connection to a catheter (not shown) implanted in the patient, and a drain line 16 for dispensing spent treatment fluid ("effluent") to a drain (now shown), for example a container or a sink. During operation, the arrangement 11 performs a fill phase in which a pumping mechanism in the APD cycler 11a actuates the cassette 12 to pump treatment fluid from the container 13 to the patient through the lines 14, 15, a dwell phase in which the treatment fluid is left within the peritoneal cavity of the patient, and a drain phase in which the spent treatment fluid is pumped to the drain through the patient and drain lines 15, 16.

As explained in the Background section, patients on PD are exposed to an elevated risk of attracting infection or inflammation in the peritoneal cavity, caused by bacteria admitted via the indwelling catheter. Often such infection or inflammation is located at the peritoneum and is denoted "peritonitis". Developed peritonitis may be manifested by the patient experiencing fever, diffuse abdominal pain, and nausea. Peritonitis represents a medical emergency, and early detection and treatment is essential to reduce morbidity and mortality in PD patients. In addition, repeated episodes of peritonitis may contribute to vascular proliferation and interstitial fibrosis, with ensuing loss of ultrafiltration capacity and therapy failure. In PD, peritonitis may be detected by extracting and analyzing the density of white blood cells (WBCs) in the effluent. According to established practice, a WBC count above 100 cells/μL in the effluent of PD is regarded as a sign of peritonitis and may result in the patient being given antibiotics.

The present disclosure relates to techniques that enable early detection of peritonitis in patients undergoing PD without the need to extract and analyze samples of the effluent. This is achieved by use of an optical detection apparatus, which is operable to produce a signal representative of the WBC count in effluent when mounted onto a tubing portion through which the effluent flows. Thus, embodiments of the invention enable remote and non-intrusive determination of the WBC count. As will be appreciated from the following description, the optical detection apparatus is not limited to detection of WBCs but is generally applicable for determination of the density of particles ("particle density") in a fluid flowing through a tubing. As used herein, "density" refers to number per unit volume and may be equivalent to concentration.

In FIG. 1, the optical detection apparatus is represented by reference numeral 20 and comprises a measurement device 21, which is mounted onto the drain line 16, and an analysis device 22 which configured to receive and process one or more output signals of the measurement device 21 for determination of a parameter value representative of WBC density. It is conceivable that the measurement and analysis devices 21, 22 are integrated in a single unit. In another variant, the measurement device 21 is configured to wirelessly transmit its output signal(s) to the analysis device 22, which thus may be located remotely from the measurement device 21. In a further variant, the measurement device 21 and/or the analysis device is included in the APD cycler 11a.

The measurement device 21 is mounted onto a "tubing portion" which is transparent or at least translucent. The tubing portion may be included in the drain line 16, as shown in FIG. 1, or in the patient line 15. As used herein, a "transparent" material has the property of transmitting light with little scattering so that objects are clearly visible through the material, and a "translucent" material has the property of permitting passage of light while diffusing it so that objects are not clearly visible through the material. Commonly, the tubings in the disposable 11b are made of transparent or translucent material. The tubing portion may thus be an integral part of the drain line 16 or patient line 15. However, should the line 16/15 be made of opaque material, the tubing portion may be a separate tubing of transparent or translucent material that is spliced into the line 16/15. Thus, in some embodiments, the tubing portion has a rounded or at least non-rectangular cross-section and is made of flexible material. However, it is also conceivable that the tubing portion is a specialized cavity or chamber that is installed in the line 16/15 to facilitate the measurements by measurement device 21. Such a specialized cavity may be or comprise a cuvette with planar optical surfaces of transparent material.

In some embodiments, the optical detection device 20 may be arranged to communicate with the APD cycler 11a. For example, the optical detection device 20 may receive, from the APD cycler 11a, a signal that indicates start of a drain phase and thereby presence of effluent in the drain line 16. Alternatively or additionally, the signal from the APD cycler 11a may trigger the optical detection device 20 to measure particle density. It is also conceivable that the optical detection device 20 transmits a signal indicative of the measurement result to the APD cycler 11a, which may operate a feedback unit to inform a user thereof.

The following discussion is based on the presumption that the tubing portion has the same properties as ordinary tubing included in the disposable 11b, for example by being flexible and transparent/translucent and having a rounded cross-section. For simplicity of notation, the tubing portion will hereinafter be referred to as "tubing 16".

As will be described in detail below, the measurement device 21 is configured to generate its output signal(s) by illuminating the effluent that flows through the tubing 16 and by detecting light that is transmitted by and/or scattered by the effluent. The present Applicant has identified some inherent difficulties with this approach, including but not limited to: 1) light scattering by the tubing may introduce a significant and unknown disturbance in the output signal(s), 2) the optical properties and thus the output signal(s) may vary between different locations on a tubing and between different tubings, 3) the generally curved cross-sectional shape of tubing acts as a cylindrical lens to refract light that enters and leaves the tubing, thereby imposing strict requirements on the accuracy and consistency in the positioning of detection equipment, 4) the shape of the tubing may change over time, potentially resulting in a drift in the output signal(s), and 5) presence of air bubbles in the effluent may introduce a significant and unknown disturbance in the output signal(s). Many of these difficulties may be overcome with careful, and possibly frequent, calibration of the measurement device 21. However, such calibration makes deployment difficult and time consuming and may require the optical detection apparatus 20 to be installed and operated by trained personnel.

Figure 2:
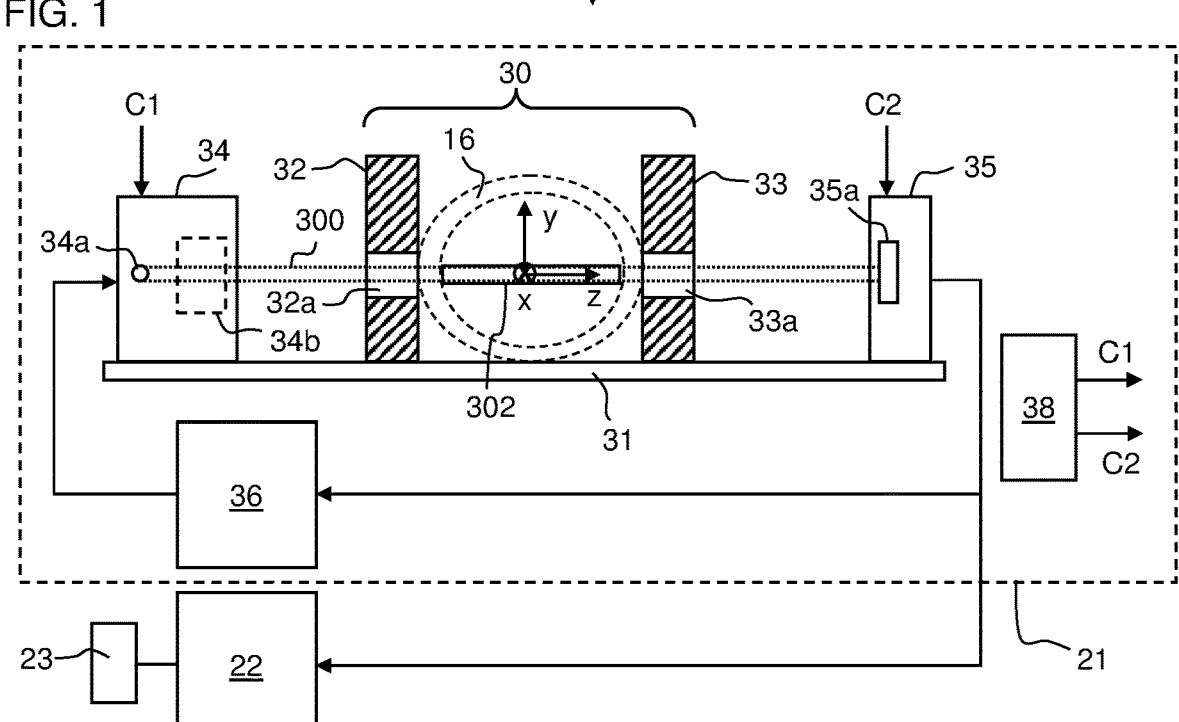
FIG. 2 is a side view, partly in section, of an example optical detection apparatus.

Embodiments described herein take a different approach that mitigates or even eliminates the need for calibration. Before describing this approach in detail, an example of the optical detection apparatus 20 will be described with reference to the elevated side view in FIG. 2. The measurement device 21 is outline by dashed lines and comprises a holder 30, a light emitting device 34 and a light detecting system 35, which are mounted onto a common base plate or platform 31. The provision of a common platform 31 facilitates assembly of the measurement device 21 with proper alignment between the holder 30, the light emitting device 34 and the light detecting system 35. The platform 31 also improves the robustness of the device 21 to mechanical shock and stress. The holder 30 comprises first and second walls ("holding elements") 32, 33 which define a slot for receiving the tubing 16 (schematically indicated by dashed lines). The spacing between the walls 32, 33 is equal to or smaller than the outer diameter of the tubing, which typically is about 5-15 mm, so that the tubing 16 is squeezed, frictionally held or otherwise fixed in the holder 30. At least part of the respective wall 32, 33 is transparent or translucent. In the example of FIG. 2, which shows walls 32, 33 in cross-section, the respective wall 32, 33 defines a through-hole or opening 32a, 33a. In some embodiments, transparent/translucent windows may be arranged in the openings 32a, 33a.

The light emitting device 34 comprises a light source 34a, which is configured to emit a light beam 300 in the ultra-violet, visible or infrared wavelength range. The light source 34 may comprise a light-emitting diode (LED) or a minia-turized laser device such as a laser diode. In some embodiments, the light emitting device 34 further comprises beam-forming optics 34b, which may be arranged to focus the light beam 300 inside the holder 30, for example at a nominal location halfway between the walls 32, 33. Alternatively or additionally, the beam-forming optics 34b may be config-ured to achieve a predefined transverse beam profile of the light beam 300. As shown, the light emitting device 34 is aligned with the walls 32, 33 so that the light beam 300 passes the openings 32a, 32b. The light beam 300 thereby defines a target volume 302 inside the tubing 16. In FIG. 2, a cartesian coordinate system is arranged at the center between the walls 32, 33, with the z axis extending along the light beam 300, the y axis extending transverse to both the light beam 300 and the longitudinal extent of the tubing 16, and the x axis extending parallel to the longitudinal extent of the tubing 16.

The light detecting system 35 comprises a light detecting device ("detector") 35a, which is responsive to the emitted light. In the illustrated example, the detector 35a is arranged to detect transmitted light and is thus aligned with the light beam 300. In some embodiments (not shown), the light detecting system 35 may comprise detection optics to direct incoming light onto the detector 35a. The light detection system 35 is operable to generate an output signal repre-sentative of the amount of incident light on the detector 35a. The output signal is time-varying and comprises signal values that represent the momentary amount of incident light at different times. In the illustrated example, the measure-ment device 21 further comprises a power controller 36, which is configured to generate a power control signal for the light emitting device 34 based on the output signal of the detector 35a.

The overall operation of the measurement device 21 is controlled by a control unit 38, which may be configured to generate a control signal C1 for the light emitting device 34 and a control signal C2 for the light detecting system 35. The control signals C1, C2 may control activation of the light source 34a and the detector 35a, respectively.

In the example of FIG. 2, the analysis device 22 is connected to a feedback unit 23, which may be operable to generate visible, audible, or tactile feedback to the patient and/or a caretaker. The feedback unit 23 may thus comprise one or more of a display, an indicator lamp, a speaker, a buzzer, a beeper, a vibrator, etc. The analysis device 22 may be configured to present the outcome of its analysis on the feedback device 23, for example as one or more parameter values representative of WBC count, an indication of a potential infection or inflammation, etc. The feedback unit 23 may or may not be included in the APD cycler 11a.

The deployment and operation of the optical detection apparatus 20 will be described with reference to an example method 500 represented by a flow chart in FIG. 5. The method 500 comprises a step 501 of arranging a portion of the tubing 16 in the holder 30. Step 500 may be performed by the patient or a caretaker at any time during a PD treatment session, or in advance thereof. In step 502, the light emitting device 34 is operated to irradiate the target volume 302 inside the tubing 16, by generating the light beam 300. In step 503, the light detecting device 35 is operated to receive light from the target volume 302 while the target volume is illuminated by the light beam 300. As a result of step 503, the light detecting system 35 generates a time-dependent output signal representative of the amount of light received by the light detecting system 35 from the target volume 302 as a function of time. Steps 502-503 may be performed by the control unit 38 generating the control signals C1, C2 with proper timing.

In step 504, the time-dependent output signal is processed for determination of a current value of a TV parameter representative of the temporal variability (TV) in the output signal. As used herein, "temporal variability" designates the magnitude of variations over time in a signal, and specifi-cally the magnitude of variations resulting from the illumi-nation of the target volume 302. The TV parameter is computed based on signal values in a time segment of the output signal. Step 504 may be seen to estimate the particle density in the fluid flowing through the tubing 16, since the TV parameter has been found to represent particle density (see below). In some embodiments, step 504 may use the current value as an estimate of the particle density. In other embodiments, step 504 may convert the current value into an actual density value, for example by use of predefined relation (cf. FIG. 8). Step 504 may be followed by a step 505 of evaluating the estimated particle density, for example in relation to one or more threshold levels for detection of infection/inflammation. Based on the outcome of the evalu-ation, step 505 may operate the feedback unit 23 (FIG. 2) to generate an alert. Alternatively or additionally, step 505 may operate the feedback unit 23 to present the estimated particle density to the patient or caretaker. Alternatively or addition-ally, step 505 may store the estimated density in a local or remote computer memory. Steps 504-505 may be performed by the analysis device 22 in FIG. 2. In the context of FIGS. 1-2, detected particles mainly comprise WBCs and, possibly, occasional air bubbles.

The example method 500 is the result of considerable experimental effort. Experiments have revealed a relation between temporal variability in an output signal that repre-sents transmitted or scattered light from a target volume in a moving fluid inside a tubing and the particle density in the moving fluid. One explanation of this phenomenon may be that individual particles that enter the target volume 302 give rise to a momentary signal response in the output signal, in the form of a decrease if the output signal represents transmitted light, and a momentary increase if the output signal represents scattered light. Thus, independent of detec-tion technique (transmission/-scattering), particles passing the target volume 302 result in peaks in the output signal. With increasing density of particles, the number of peaks in the output signal per unit time and/or the magnitude of the peaks will increase, which in turn corresponds to an increased temporal variability in the output signal. The example method 500 is at least useful for density assessment in fluids with a particle density of less than 2000, 1000, 500 or 200 particles per microliter (μL). It is realized that the method 500 is suitable for detection of WBCs in PD effluent, since infection/inflammation in PD patients is inferred already when the WBC count is at or above 100 per microliter. The example method 500 is currently believed to be less suitable for measurements on highly turbid fluids, which will severely attenuate the light beam 302 and thereby potentially cause the peaks to be embedded in signal noise.

The example method 500 is at least useful for measurement in fluids with particles having an average size of less than 50, 40, 30 or 20 micrometers. The method 500 is thereby suitable for detection of WBCs in PD effluent, since WBCs have an average size of about 10 micrometers.

The example method 500 has been found to be relatively insensitive to light scattering caused by the tubing itself, for example by surface structures on the outside of the tubing or irregularities in the material of the tubing wall. Such light scattering by the tubing mainly contributes to a baseline in the output signal, and variations in the light scattering properties at different locations on the tubing or between different tubings mainly shift the baseline, whereas the temporal variability in relation to the baseline is largely unaffected by such variations. Thereby, the method 500 is relatively robust and may be deployed without calibration.

Figure 7A:
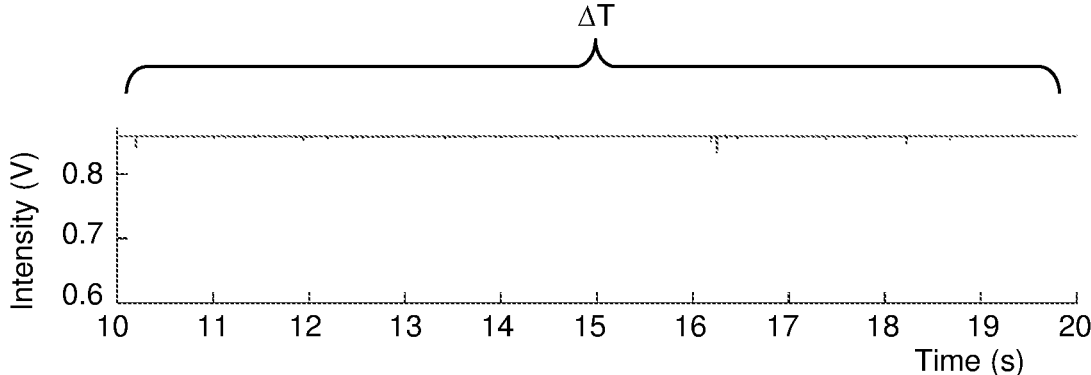
FIGS. 7A-7C are graphs of transmitted light intensity measured for a fluid with a density of 0, 100 and 1000, respectively, white blood cells per microliter.
Figure 7B:
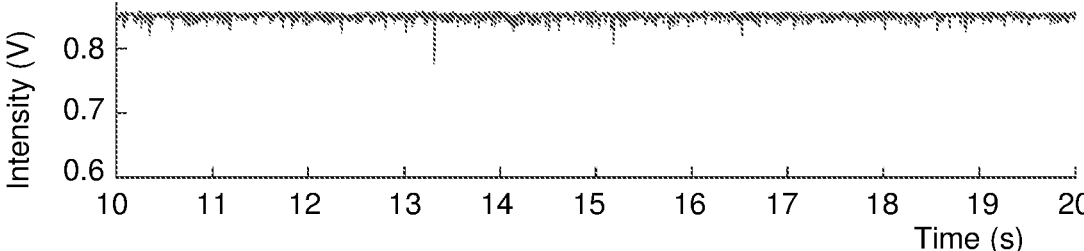
Figure 7C:
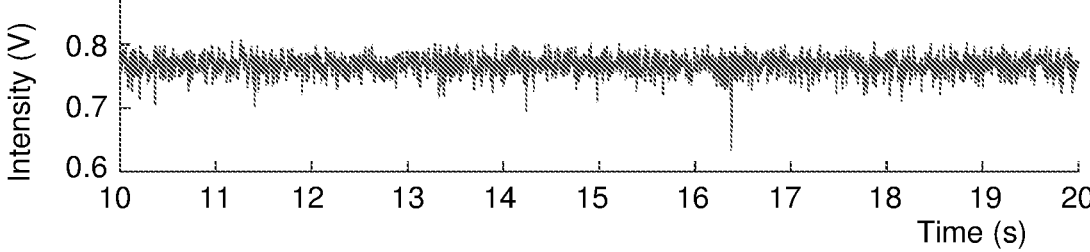

FIGS. 7A-7C show examples of output signals generated by a detector arranged to receive transmitted light, for example as shown in FIG. 2, for different densities of WBCs in the effluent from an APD arrangement (cf. 11 in FIG. 1). Each signal value in the output signal represents the amount of light detected by the detector during a detection period, also known as "integration period". FIG. 7A is generated for a fluid with a WBC count of 0 cells/μL. As seen, the output signal has a low temporal variability and a baseline that is stable over time. FIG. 7B is generated for a fluid with a WBC count of 100 cells/μL. The temporal variability has increased but the baseline of the signal remains stable and is substantially the same as in FIG. 7A. FIG. 7C is generated for fluid with a WBC count of 1000 cells/μL. The temporal variability has increased even further, and the baseline of the signal remains stable over time. It is also seen that the level of the baseline has decreased compared to FIG. 7B, indicating that the particle density is so large that the light beam is notably attenuated. It is clear from FIGS. 7A-7C that the temporal variability in the output signal during a measurement time is representative of the particle density. An example of such a measurement time ΔT is indicated in FIG. 7A. The measurement time may span all or part of a drain phase, and the TV parameter may be generated to represent one or more measurement periods. For example, the TV parameter may be calculated as an average of the temporal variability of the output signal within two or more measurement periods during a drain phase.

Further experimentation has revealed various functional and structural modifications of the measurement device 21, which may serve to improve the estimation of particle density. These modifications, represented as embodiments, are described in the following.

In some embodiments, the source 34a is a laser that emits coherent and mono-chromatic light in a substantially collimated beam. Compared to non-coherent light sources, lasers have higher radiance or brightness and enables more energy for inter-action with the particles in the target volume 302. The laser beam will provide a well-defined target volume 302. It may be challenging to achieve a sufficient signal response in the output signal when the target volume 302 is small, for example inside a tubing 16. This may be facilitated by the high radiance of laser light.

In some embodiments, the laser may emit light at a wavelength that causes particles in the fluid to emit light, for example by photoluminescence such as fluorescence or phosphorescence. By detecting the emitted light by the light receiving system 35, the techniques described herein may be applied to determine the density of a specific type of particles in the fluid. In the context of the present disclosure, such emitted light is encompassed in the term "scattering".

In some embodiments, the laser may emit the light at two or more wavelengths at which the particles are known to exhibit different absorption properties. By detecting transmitted light at the two of more wavelengths by the light receiving system 35, the techniques described herein may be applied to determine the density of a specific type of particles in the fluid.

In some embodiments, the light emitting device 34 is configured to irradiate the target volume 302 by pulsed light. The use of pulsed light enables the impact of ambient light on the measurement to be suppressed, if the light detecting system 35 is operated to detect light during and between light pulses, respectively. Thereby, the light detected between light pulses represents ambient light and may be subtracted from the light detected during light pulses to substantially remove the influence of ambient light. Such subtraction may be performed by the light detection system 35 or the analysis device 22.

In some embodiments, the light emitting device 34 is configured to generate a light beam 300 with a focus at the approximate center of tubing 16 when installed in the holder 30 (cf. FIG. 2). Focusing the light beam increases the radiance of the light beam inside the tubing 16. Further, by focusing the light beam, the transverse dimensions or cross-sectional area of the target volume 302 may be set in relation to the particles to be detected. Still further, by focusing the light, the cross-sectional area of the light beam when entering the tubing 16 is reduced and the impact of the above-mentioned lens effect is mitigated.

In some embodiments, the light emitting device 34 is configured to define the target volume 302 to have a transverse cross-sectional area of less than $10^5$, $10^4$, $10^3$, $10^2$ or 10 times the cross-sectional area of the individual particle. It is currently believed that performance is improved with decreasing transverse cross-sectional area of the target volume 302, since the magnitude of the peaks in the output signal is likely to increase with decreasing area ratio. However, acceptable performance is at least attained with an area ratio of $10^5$ between target volume and particles. The cross-sectional area of the target volume 302 refers to its largest transverse dimensions within the tubing 16. The transverse dimensions may be given by any conventional measure, such as FWHM (full width at half maximum). For example, the output signals in FIGS. 7A-7C are generated for a focused laser beam with transverse dimensions of 2.3 mm (x direction in FIG. 2) and 1.3 mm (y direction in FIG. 2). At the inner surfaces of the tubing (FIG. 2), these dimensions are slightly larger, approximately 2.5 mm×1.5 mm.

In some embodiments, the light detecting system 35 is operated to detect incoming light during a sequence of detection periods, where each detection period results in a signal value in the output signal. The minimum time between starts of detection periods may be set in relation to the expected or actual flow rate of the fluid through the tubing 16. Refer to FIG. 3B, which illustrates a particle 303 that traverses the target volume 302 at speed Vx. The speed Vx is approximately given by the ratio between the flow rate F and the cross-sectional area A of the tubing 16, F/A. The target volume 302 has a transverse width of Wx. To ensure that one and the same particle is only detected within the target zone 302 in one of the detection periods, the minimum time should exceed Wx/Vx, i.e. Wx·A/F. The actual time between starts of detection periods may be set to exceed the minimum time while being small enough to yield a sufficient number of signal values during a predefined measurement period (cf. AT in FIG. 7A), for example to achieve a sufficient accuracy of the TV parameter.

In some embodiments, for example as exemplified in FIG. 2, the light detecting system 35 comprises a detector 35a which is aligned with the light emitting device 34 to receive light transmitted through the target volume 302 and generate an output signal representative of transmitted light. Detection of transmitted light is simple to implement and results in a well-defined output signal.

Figure 3A:
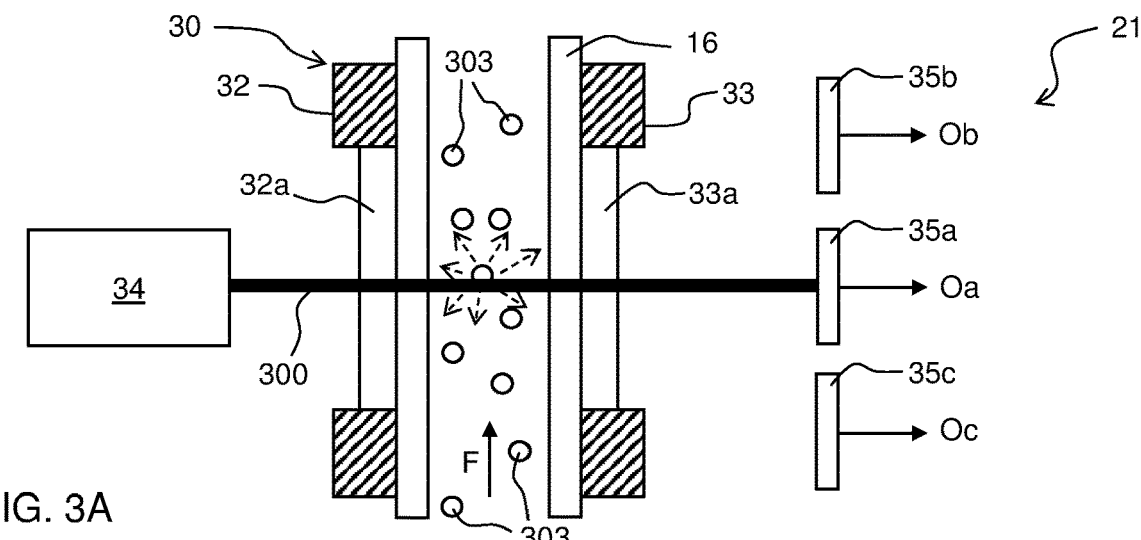
FIG. 3A is a section view of an arrangement in an example optical detection apparatus.

In some embodiments, instead of or in addition to detecting transmitted light, the light detecting system may comprise a detector which is arranged to receive light scattered from the target volume and generate a second output signal representative of the amount of scattered light. An example is shown in FIG. 3A, which is a view of a cross-section of a measurement device 21 comprising three detectors 35a-35c. A first detector 35a is arranged to detect transmitted light and generate output signal Oa. Second and third detectors 35b, 35c are arranged to detect scattered light and generate output signals Ob, Oc. As indicated by dashed arrows in FIG. 3A, light is scattered by a particle 303 that interferes with the light beam 300. Compared to detection of transmitted light, detection of scattered light is less sensitive to changes in the position of the detector and may thus be more robust to mechanical shock.

Using two of more detectors for detecting scattered light, for example as shown in FIG. 3A, has the advantage of increasing the number of available output signals that comprise corresponding information about the presence of particles. It is understood that step 504 may process more than one output signal to generate the TV parameter and that the accuracy of the TV parameter may be improved with increasing number of output signals. Similarly, using two or more detectors for detecting scattered light and transmitted light, for example as shown in FIG. 3A, may provide equal advantages.

In embodiments that comprise a first detector for detecting transmitted light and a second detector for detecting scattered light, the second detector may be displaced along the longitudinal extent of the tubing in relation to the first detector. By combined processing of the output signals from the first and second detectors, the impact of any lens effect of the tubing may be mitigated. One such embodiment is exemplified in FIG. 3A, where detectors 35b and 35c are displaced from detector 35a along the extent of the tubing 16. It is understood that the lens effect of the tubing 16 mainly causes spreading of the light beam 300 in a plane transverse to the longitudinal extent of the tubing 16, i.e. perpendicular to the drawing plane in FIG. 3A. Since the detectors 35b, 35c are arranged outside this plane, their output signals are largely unaffected by the lens effect.

In some embodiments, the tubing may be deformed into a flattened shape to mitigate the lens effect of the tubing. An example of such an embodiment is shown in FIG. 4, which is a side view of a holder 30 with an installed tubing 16 (shown in cross-section), which is flattened while defining an internal channel 16c through which the fluid flows. In the illustrated example, the holder 30 is configured to deform the tubing 16 to define first and second wall portions 16a, 16b, which are spaced apart and substantially planar. Although not shown in FIG. 4, the first wall portion 16a faces the light emitting device 34 and the second wall portion 16b faces the light detecting system 35. It is realized that by aligning the light emitting device 34 and the light detecting system 35 with the wall portions 16a, 16b, the lens effect of the tubing will be reduced or even eliminated. To further reduce refraction of the light beam 300, the holder 30 may be configured to arrange the wall portions 16a, 16b substantially parallel, for example as shown in FIG. 4.

In some embodiments, the walls 32, 33 of the holder 30 are configured to define the flattened shape of the tubing, for example as shown in FIG. 4. The walls 32, 33 may be fixed to define a transverse slot ("mounting space") that is smaller than the outer transverse diameter of the tubing 16, so that the tubing 16 attains a flattened shape when it is pressed into the slot. Alternatively, as shown in FIG. 4, at least one of the walls 32, 33 may be moveable to expand the slot for insertion of the tubing 16 and to contract the slot and thereby deform the inserted tubing 16. In the example of FIG. 4, the wall 33 is moveable parallel to the platform 31, as indicated by a double-ended arrow. Further, the holder 30 comprises a biasing mechanism 40 that applies a biasing force on wall 33 towards wall 32. In the illustrated example, the walls 32, 33 and the biasing mechanism 40 are mounted on a plate 31a, which is turn is fixed to the platform 31. The biasing mechanism 40 comprises a guiding pin 41, which is arranged to extend into a corresponding hole 42 in the wall 33, and a spring 43, which is arranged around the guiding pin 41 to provide the biasing force. The wall 33 is arranged to slide on the plate 31a into engagement with a stop 44, subject to the biasing force.

In some embodiments, the walls 32, 33 define through-holes for the light beam 300, for example shown in FIG. 2. This may reduce the amount of stray light received by the light detecting system 35. In other embodiments, the holder 30 comprises trans-parent/translucent windows 32a, 33a for engagement with the tubing 16 to define the first and second wall portions 16a, 16b, for example as shown in FIG. 3. This has been found facilitate the attainment of a substantially planar shape of the wall portions 16a, 16b and also to stabilize the planar shape over time.

Although not shown in the drawings, the holder 30 may comprise a top closure, for example in the form of a lid, which may be secured to the walls 32, 33 after installation of the tubing 16. This may serve to stabilize the position of the tubing 16 over time, for example to prevent the tubing 16 from slipping out of the slot between the walls 32, 33.

In some embodiments, for example as shown in FIG. 3A, the light emitting device is arranged with the light beam 300 substantially perpendicular to the longitudinal extent of the tubing 16. This may facilitate assembly of the measurement device 21 since the light emitting device 34 and the light detection system 35 may be simply aligned with the holder 30.

In some embodiments, as shown in FIG. 2, the measurement device 21 further comprises a control device ("power controller") 36 for the light emitting device 34, where the power controller 36 is configured to adjust an output power of the light emitting device 34 so as to substantially maintain the baseline of the output signal at a predefined value. The stabilization of the baseline has been found to significantly improve performance. Recalling that the baseline includes light scattering caused by the tubing, it is understood that stabilization of the baseline by adjustment of the output power of the light emitting device 34 counteracts the impact of spatial and/or temporal variations in properties of the tubing, such as shape, surface structure, optical properties, etc. The stabilization of the baseline effectively obviates the need for calibration.

The power controller 36 may implement any form of feedback control, such as P, PI or PID, to stabilize the baseline. In this feedback control, the power controller 26 may obtain a current baseline value and operate a feedback loop to minimize the difference between the current baseline value and a set value for the baseline. The current baseline value may be computed as a mean, median, maximum or minimum value within a time window in the output signal. Depending on implementation, the power detector 36 may compute the current baseline value in the output signal (cf. FIG. 2) or otherwise obtain the current baseline value, for example from the analysis device 22.

The power controller 36 may be configured to adjust the output power of the light emitting device 34 at the start of a measurement period (cf. AT in FIG. 7A), or continuously or intermittently throughout the measurement period.

Figure 6:
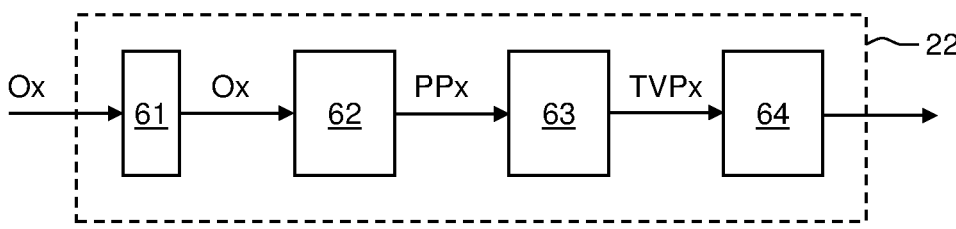
FIG. 6 is a block diagram of an example analysis device in an optical detection apparatus.

FIG. 6 is a block diagram of an example analysis device 22. In FIG. 6, the time-dependent output signal from the measurement device 21 is designated by Ox and may, for example, correspond to one or more of the signals Oa-Oc in FIG. 3A. In the illustrated example, the analysis device 22 comprises an input block ("module") 61 which is configured to receive the signal Ox. A preprocessing block 62 is configured to operate on Ox to generate a corresponding time-dependent preprocessed signal PPx. A parameter calculation block 63 is configured to process PPx to generate one or more values of the TV parameter, TVPx, for example in accordance with step 504 in FIG. 5. If Ox comprises two or more output signals, the preprocessing block 63 may generate TVPx for the respective output signal or an aggregated TVPx for the output signals. A postprocessing block 64 is configured to perform step 505 in FIG. 5. For example, the block 64 may be configured to evaluate TVPx for detection of infection/inflammation and, based thereon, selectively provide a control signal to the feedback unit 23 (FIG. 2).

Further experimentation has revealed various functional and structural modifications of the analysis device 22, which may serve to improve the estimation of particle density. These modifications, represented as embodiments, are described in the following.

In some embodiments, the preprocessing block 62 is configured to perform a high-pass (HP) filtering of Ox when generating PPx. The HP filtering may mitigate the effect of drifts in the baseline of Ox over time. Such drifts may occur when the tubing is deformed by the holder 30, for example as shown in FIG. 4. It may take some time for the tubing 16 to adapt from its original cylindrical shape to the flattened shape, and the adaptation has been found to potentially cause a drift in the baseline of Ox. The adaptation may proceed for more than one hour, which unfavorably delays the start of the measurement. This delay may be overcome by performing HP filtering to suppress the drift in Ox.

Any type of HP filter may be used, including but not limited to finite impulse response (FIR) filters such as Kaiser window filters, least-squares filters and equiripple filters, or IIR (infinite impulse response) filters such as Butterworth filters, Chebyshev filters and elliptic filters. In one non-limiting example, the cut-off frequency of the HP filter may be approximately 1 Hz.

Conventional HP filters tend to introduce ringing into the filtered signal after large signal changes and may thus be less suitable for use in the preprocessing block 62, recalling that Ox potentially comprises numerous peaks (signal changes) corresponding to particles entering the target volume.

In one embodiment, which obviates the risk for ringing, the HP filtering performed by the preprocessing block 62 comprises determining a temporal envelope for Ox, and computing a difference signal between the temporal envelope and Ox, whereupon PPx is generated from the difference signal. The difference signal may be computed by time-aligning Ox and the temporal envelope, and by computing differences between values in the temporal envelope and corresponding values in Ox. If Ox represents scattered light (cf. Ob, Oc in FIG. 3A), the lower temporal envelope of Ox may be computed and subtracted from Ox to yield a HP filtered signal. If Ox represents transmitted light (cf. Oa in FIG. 3A), the upper temporal envelope may be computed, and Ox may be subtracted from the upper temporal envelope. In this way, Ox is both HP filtered and inverted in one operation. The temporal envelope may be determined by any conventional signal processing technique, as readily available to the person skilled in the art, for example by extraction of selected peak values from the signal or by operating a Hilbert transformer on the signal.

The parameter calculation block 63 may be configured to compute TVPx from PPx (or Ox if block 62 is omitted) in many different ways. In one example, block 63 may be configured to count the number of peaks in PPx/Ox during the measurement period (cf. ΔT in FIG. 7A). Such a measure of temporal variability may need to be normalized by the flow rate in the tubing 16 during the measurement period. Further, it may be difficult to infer if two or more particles are present in the target volume 302 during one detection period.

In another example, block 63 may be configured to determine TVPx as a function of the energy content in PPx/Ox during the measurement period. The energy may be assumed to be proportional to the particle density. In signal processing, the energy E in a discrete-time signal x(n) may be defined as, with N being the number of samples within the measurement period:

$$E = \sum_{n=1}^{N} |x(n)|^2$$

It may be assumed that the energy in both scattered light and transmitted light increases linearly with particle density. As seen from FIGS. 7A-7C, the baseline of Ox is independent of particle density for low particle densities and is instead dependent on other conditions, for example scattering by the tubing. The energy $E_c$ originating from particles passing the target volume may be computed by removing the baseline, for example given by the mean x̄ of x(n):

$$E_c = \sum_{n=1}^{N} |x(n) - \bar{x}|^2$$

The energy in a signal depends on its length N. Dividing $E_c$ with N results in a measure of the average energy per sample, which in this case is the same as the variance $\sigma^2$ in the signal. Thus, in another example, block 63 may be configured to determine TVPx as a function of the variance or a related measure such as standard deviation, coefficient of variation, or variance-to-mean of the signal.

In a further example, block 63 may be configured to determine TVPx as a function of the entropy in Ox/PPx.

Figures 8, 9A, 9B, 9C:
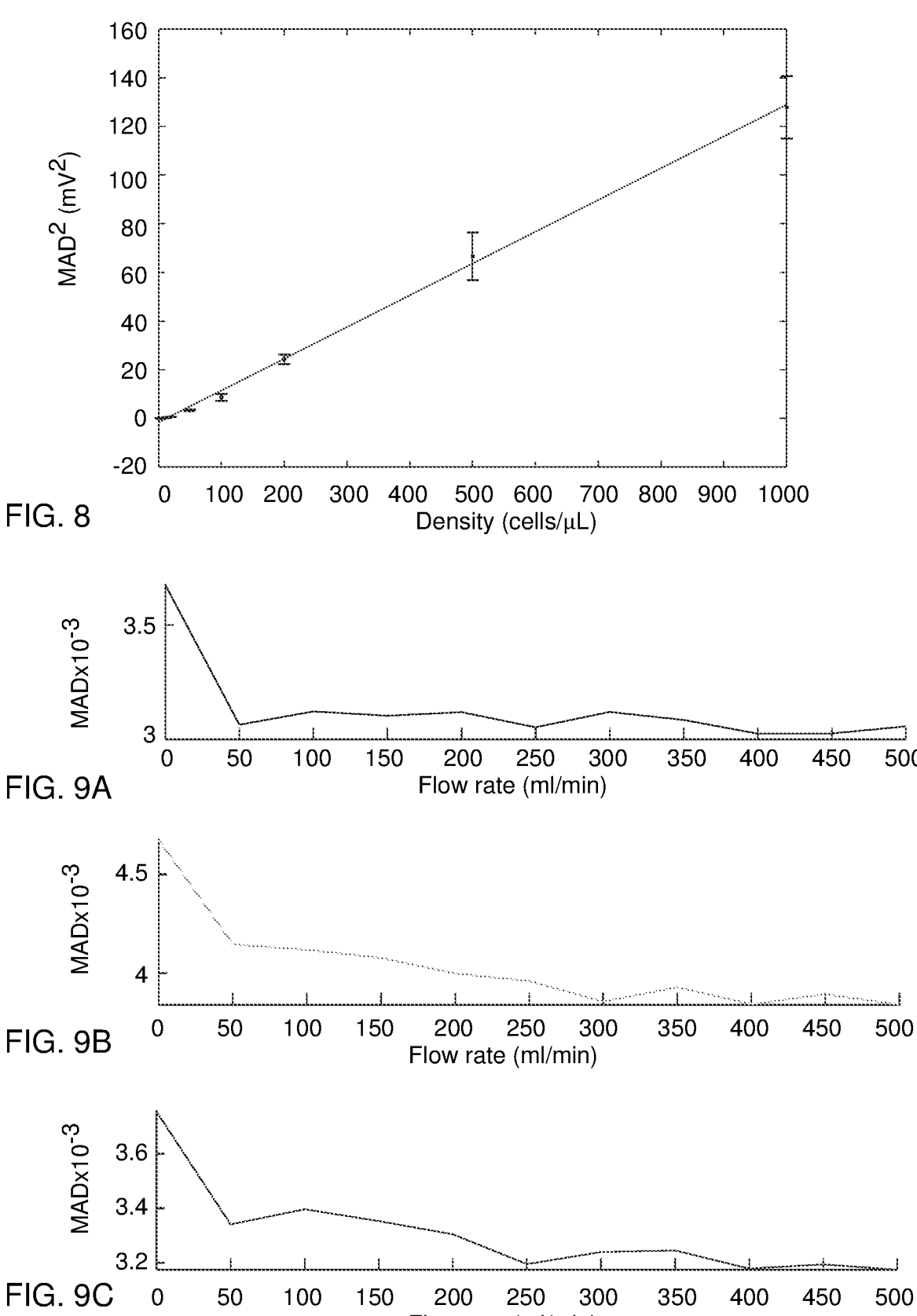
FIG. 8 is a graph of measured temporal variability, given by MAD squared, as a function of particle density.
FIGS. 9A-9C are graphs of temporal variability, given by MAD, as a function of flow rate for output signals generated by the arrangement in FIG. 3A.

As noted in the foregoing, occasional air bubbles in the fluid may disrupt the measurements of particle density. Such air bubbles may generate large peaks in the output signal and may thus have a significant impact on TVPx. To mitigate the impact of air bubbles, it may be advantageous to determine TVPx as a function of a measure that is robust to outliers. One such measure is Median Absolute Deviation (MAD): MAD=median(x(n)−x̃), where x̃ is the median of x(n) and n∈1 . . . N. In a variant, x̃ may be replaced by x̄, i.e. the mean of x(n). In a further alternative, MAD may designate Mean Absolute Deviation: MAD=mean(x(n)−x̃) or MAD=mean(x (n)−x̃). Irrespective of definition, MAD is related to the square root of the average energy in the signal, and therefore $MAD^2$ may be proportional to particle density. FIG. 8 is a plot of $MAD^2$ computed in output signals obtained for fluids with different WBC counts in the range 0-1000 cells/μL. As seen, $MAD^2$ is proportional to particle density. This relation holds for other energy-based measures, for example as exemplified in the foregoing.

Theoretically, energy-based measures should be independent of flow rate, since changes in flow rate will only change the frequency content of the output signal, not the magnitude of its variability. FIGS. 9A-9C show MAD computed in output signals from the detectors 35a-35c in FIG. 3A at different flow rates in the range 0-500 ml/min. As seen, for all flow rates above 0, MAD is indeed substantially independent of flow rate, both for transmitted light (FIG. 9A) and scattered light (FIGS. 9B-9C).

In some embodiments, as an alternative or supplement to the above-mentioned use of the power controller 36 (FIG. 2) to stabilize the baseline, block 62 may be configured to estimate the baseline for the measurement period and perform a normalization by the estimated baseline. For example, the baseline may be estimated by the mean, median, maximum, or minimum of Ox/PPx within the measurement period.

Figure 10:
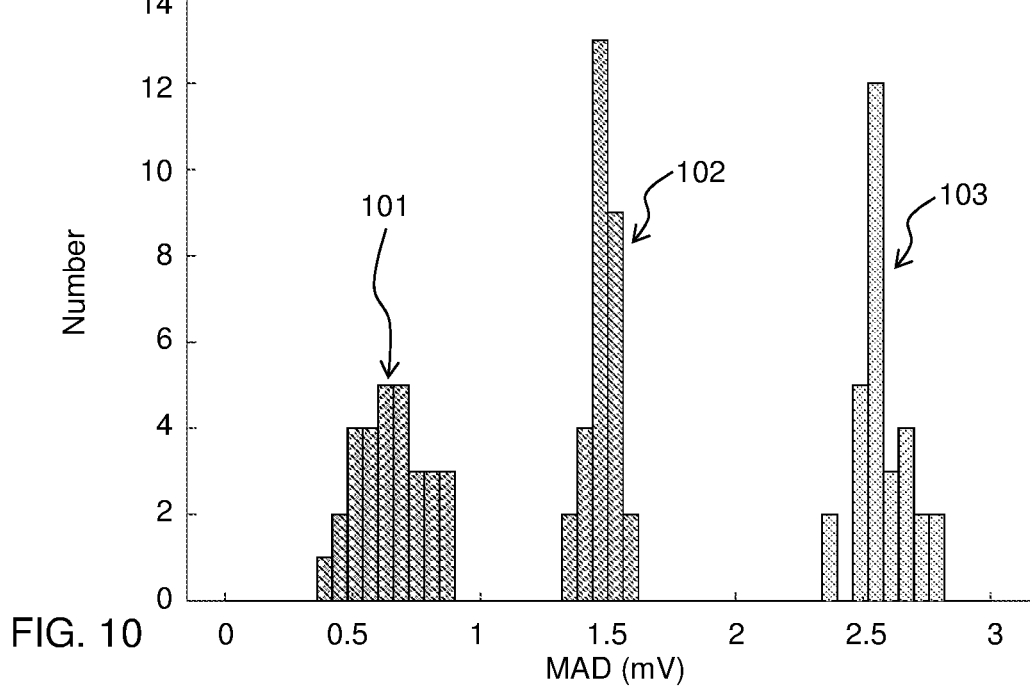
FIG. 10 is a histogram of the distribution of temporal variability, given by MAD, measured through 30 different tubings containing in a fluid with a density of 0, 50 and white blood cells per microliter.

To further demonstrate the utility of the example method 500, FIG. 10 is a histogram of MAD values computed for output signals representing transmitted light, after HP filtering by envelope subtraction, where the output signals were generated for 30 different tubings and for three different densities of WBCs in the fluid: 0, 50, 100 cells/μL. As seen, the MAD values form three distinct groups 101-103, where group contains MAD values for 0 cells/μL, group 102 contains MAD values for 50 cells/μL, and group 103 contains MAD values for 100 cells/μL. Clearly, it is possible to discriminate between these densities of WBCs and thereby reliably signal a risk for inflammation/infection, irrespective of the tubing used.

While the subject of the present disclosure has been described in connection with what is presently considered to be the most practical embodiments, it is to be understood that the subject of the present disclosure is not to be limited to the disclosed embodiments, but on the contrary, is intended to cover various modifications and equivalent arrangements included within the spirit and the scope of the appended claims.

For example, the techniques described in the foregoing are not limited to APD but are equally applicable to other types of PD therapy such as CAPD. The techniques are not limited to detection of WBC density in PD effluent but are equally applicable to detection of WBC density in other medical fluids. The techniques are not limited to WBCs but are equally applicable to other particles, for example other types of cells. In one example, the techniques are applicable for detecting red blood cells in dialysis fluid flowing through a tubing in a hemodialysis machine, where an increased particle density may signal leakage of blood into the dialysis fluid. In another example, the techniques are applicable to inferring if a tubing contains liquid or gas, or to inferring presence of gas bubbles in a fluid flowing through a tubing.

Further, while operations are depicted in the drawings in a particular order, this should not be understood as requiring that such operations be performed in the particular order shown or in sequential order, or that all illustrated operations be performed, to achieve desirable results.

In the following, items are recited to summarize some aspects and embodiments as disclosed in the foregoing.

Item 1: An optical detection apparatus for detecting particles in a fluid flowing through a tubing (16) comprising a tubing portion of transparent or translucent material, said optical detection apparatus comprising:

a holder (30) for the tubing portion;

a light emitting device (34) configured to irradiate a target volume (302) inside the tubing portion when arranged in the holder (30);

at least one light receiving device (35a-35c) configured to receive light from the target volume (302) when irradiated by the light emitting device (34) and generate one or more time-dependent output signals (Oa-Oc) indicative of the received light; and a computation device (22) configured to process the one or more time-dependent output signals (Oa-Oc) to estimate a density of the particles in the fluid, wherein the computation device (22), to estimate the density, is configured to determine a parameter value indicative of temporal variability in the one or more time-dependent output signals (Oa-Oc).

Item 2: The optical detection apparatus of item 1, which is configured to generate a momentary signal response in the one or more output signals (Oa-Oc) for individual particles that enter the target volume (302).

Item 3: The optical detection apparatus of item 1 or 2, wherein the light emitting device (34) comprises a laser (34a) which is operable to irradiate the target volume (302).

Item 4: The optical detection apparatus of any preceding item, wherein the light emitting device (34) is configured to define the target volume (302) to have a transverse cross-sectional area of less than $10^5$, $10^4$, $10^3$, $10^2$ or 10 times an individual cross-sectional area of the particles.

Item 5: The optical detection apparatus of any preceding item, wherein the light emitting device (34) is configured to irradiate the target volume (302) by pulsed light.

Item 6: The optical detection apparatus of any preceding item, wherein the particles have an average size of less than 50, 40, 30 or 20 micrometers.

Item 7: The optical detection apparatus of any preceding item, wherein the particles comprise white blood cells.

Item 8: The optical detection apparatus of item 7, wherein the fluid comprises a peritoneal dialysis effluent.

Item 9: The optical detection apparatus of item 8, wherein the computation device (22) is configured to signal a risk for infection or inflammation if the density of the white blood cells in the peritoneal dialysis effluent exceeds a predefined limit.

Item 10: The optical detection apparatus of any preceding item, wherein the density is less than 2000, 1000, 500 or 200 particles per microliter.

Item 11: The optical detection apparatus of any preceding item, wherein the holder (30) is configured to deform the tubing portion to attain a flattened shape with an inner passage (16c) for the fluid.

Item 12: The optical detection apparatus of any preceding item, wherein the holder (30) is arranged intermediate the light emitting device (34) and the at least one light receiving device (35a-35c), and wherein the holder (30) is configured to deform the tubing portion to define first and second wall portions (16a, 16b), which are spaced apart and substantially planar, the first wall portion (16) facing the light emitting device (34) and the second wall portion (16b) facing the at least one light receiving device (35a-35c).

Item 13: The optical detection apparatus of item 12, wherein the holder (30) comprises transparent or translucent windows (32a, 33a) for engagement with the tubing portion to define the first and second wall portions (16a, 16b).

Item 14: The optical detection apparatus of any preceding item, wherein the at least one light receiving device (35a-35c) comprises a first light receiving device (35a) which is aligned with the light emitting device (34) to receive light transmitted through the target volume (302) and generate a first output signal (Oa) representative of transmitted light.

Item 15: The optical detection apparatus of item 14, wherein the at least one light receiving device (35a-35c) comprises a second light receiving device (35b; 35c) which is arranged to receive light scattered from the target volume (302) and generate a second output signal (Ob; Oc) representative of scattered light.

Item 16: The optical detection apparatus of item 15, wherein the second light receiving device (35b; 35c) is displaced along a longitudinal extent of the tubing portion in relation to the first light receiving device (35a).

Item 17: The optical detection apparatus of any preceding item, wherein the computation device (22) is configured to perform a preprocessing to generate one or more preprocessed signals (PPx) based on the one or more time-dependent output signals (Ox), and determine the temporal variability of the one or more preprocessed signals (PPx), wherein the preprocessing comprises a high-pass filtering of the one or more time-dependent output signals (Ox).

Item 18: The optical detection apparatus of item 17, wherein the high-pass filtering comprises: determining a respective temporal envelope for the at least one time-dependent output signal, and computing a difference signal between the temporal envelope and the at least one time-dependent output signal.

Item 19: The optical detection apparatus of any preceding item, wherein the computation device (22) is configured to determine the parameter value as a function of one or more of: a number of peaks, a standard deviation, a variance, a coefficient of variation, a variance-to-mean, an energy, an entropy, a mean absolute deviation or a median absolute deviation in the one or more time-dependent output signals (Oa-Oc) or a processed version thereof.

Item 20: The optical detection apparatus of any preceding item, further comprising a control device (36) for the light emitting device (34), the control device (36) being configured to adjust an output power of the light emitting device (34) so as to substantially maintain a baseline of the at least one output signal (Oa-Oc) at a predefined value.

Item 21: A method for detecting particles in a fluid flowing through a tubing comprising a tubing portion of transparent or translucent material, said method comprising:
    arranging (501) the tubing portion in a holder;
    operating (502) a light emitting device to irradiate a target volume inside the tubing portion as arranged in the holder;
    operating (503) at least one light receiving device to receive light from the target volume when irradiated by the light emitting device and to generate one or more time-dependent output signals indicative of the received light; and
    estimating (504) a density of the particles in the fluid by processing the one or more time-dependent output signals, wherein said estimating (504) comprises determining a parameter value indicative of temporal variability in the one or more time-dependent output signals.

Item 22: An apparatus for automated peritoneal dialysis comprising the optical detection apparatus of any one of items 1-20.

The invention claimed is:

1. An optical detection apparatus for detecting particles in a fluid flowing through a tubing comprising a tubing portion of transparent or translucent material, the optical detection apparatus comprising:
    a holder for the tubing portion;
    a light emitting device configured to irradiate a target volume inside the tubing portion when arranged in the holder;
    at least one light receiving device configured to receive light from the target volume when irradiated by the light emitting device and generate one or more time-dependent output signals indicative of the received light; and
    a computation device configured to process the one or more time-dependent output signals to estimate a density of the particles in the fluid,
    wherein the at least one light receiving device comprises a first light receiving device arranged to receive light scattered from the target volume when irradiated by the light emitting device and to generate a first output signal that is representative of the scattered light; and
    wherein the computation device, to estimate the density, is configured to determine a parameter value indicative of temporal variability in the first output signal.

2. The optical detection apparatus of claim 1, which is configured to generate a momentary signal response in the one or more time-dependent output signals for individual particles that enter the target volume.

3. The optical detection apparatus of claim 1, wherein the light emitting device comprises a laser which is operable to irradiate the target volume.

4. The optical detection apparatus of claim 1, wherein the light emitting device is configured to define the target volume to have a transverse cross-sectional area of less than $10^5$ times an individual cross-sectional area of the particles.

5. The optical detection apparatus of claim 1, wherein the light emitting device is configured to irradiate the target volume by pulsed light.

6. The optical detection apparatus of claim 1, wherein the particles have an average size of less than 50 micrometers.

7. The optical detection apparatus of claim 1, wherein the particles comprise white blood cells.

8. The optical detection apparatus of claim 7, wherein the fluid comprises a peritoneal dialysis effluent.

9. The optical detection apparatus of claim 8, wherein the computation device is configured to signal a risk for infection or inflammation if the density of the white blood cells in the peritoneal dialysis effluent exceeds a predefined limit.

10. The optical detection apparatus of claim 1, wherein the density of the particles in the fluid is less than 2000, 1000, 500 or 200 particles per microliter.

11. The optical detection apparatus of claim 1, wherein the holder is configured to deform the tubing portion to attain a flattened shape with an inner passage for the fluid.

12. The optical detection apparatus of claim 1, wherein the holder is arranged intermediate the light emitting device and the at least one light receiving device, and wherein the holder is configured to deform the tubing portion to define first and second wall portions, which are spaced apart and planar, the first wall portion facing the light emitting device and the second wall portion facing the at least one light receiving device.

13. The optical detection apparatus of claim 1, wherein the at least one light receiving device comprises a second light receiving device which is aligned with the light emitting device to receive light transmitted through the target volume and generate a second output signal representative of transmitted light.

14. The optical detection apparatus of claim 1, wherein the computation device is configured to perform a preprocessing to generate one or more preprocessed signals based on the one or more time-dependent output signals, and determine the temporal variability of the one or more preprocessed signals, wherein the preprocessing comprises a high-pass filtering of the first output signal.

15. The optical detection apparatus of claim 14, wherein the high-pass filtering comprises: determining a respective temporal envelope for the first output signal, and computing a difference signal between the respective temporal envelope and the first output signal.

16. The optical detection apparatus of claim 1, wherein the computation device is configured to determine the parameter value as a function of one or more of: a number of peaks, a standard deviation, a variance, a coefficient of variation, a variance-to-mean, an energy, an entropy, a mean absolute deviation or a median absolute deviation in the first output signal or a processed version thereof.

17. The optical detection apparatus of claim 1, further comprising a control device for the light emitting device, the control device being configured to adjust an output power of the light emitting device so as to maintain a baseline of the first output signal at a predefined value.

18. A method for detecting particles in a fluid flowing through a tubing comprising a tubing portion of transparent or translucent material, the method comprising: arranging the tubing portion in a holder;

operating a light emitting device to irradiate a target volume inside the tubing portion as arranged in the holder;

operating at least one light receiving device to receive light from the target volume when irradiated by the light emitting device and to generate one or more time-dependent output signals indicative of the received light; and estimating a density of the particles in the fluid by processing the one or more time-dependent output signals, wherein the operating the at least one light receiving device comprises operating a first light receiving device to receive light scattered from the target volume when irradiated by the light emitting device and to generate a first output signal that is representative of the scattered light; and wherein the estimating comprises determining a parameter value indicative of temporal variability in the first output signal.

19. An apparatus for automated peritoneal dialysis comprising:

an optical detection apparatus for detecting particles in a fluid flowing through a tubing comprising a tubing portion of transparent or translucent material, the optical detection apparatus comprising:

a holder for the tubing portion;

a light emitting device configured to irradiate a target volume inside the tubing portion when arranged in the holder;

at least one light receiving device configured to receive light from the target volume when irradiated by the light emitting device and generate one or more time-dependent output signals indicative of the received light; and a computation device configured to process the one or more time-dependent output signals to estimate a density of the particles in the fluid, wherein the at least one light receiving device comprises a first light receiving device arranged to receive light scattered from the target volume when irradiated by the light emitting device and to generate a first output signal that is representative of the scattered light; and wherein the computation device, to estimate the density, is configured to determine a parameter value indicative of temporal variability in the first output signal.

*   *   *   *   *